(12) United States Patent
Kuebelbaeck et al.

(10) Patent No.: US 8,222,406 B2
(45) Date of Patent: Jul. 17, 2012

(54) PROCESS FOR PREPARING HETEROCYCLES

(75) Inventors: Thomas Kuebelbaeck, Dülmen (DE);
Manfred Neumann, Marl (DE);
Marianne Omeis, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 351 days.

(21) Appl. No.: 12/564,509

(22) Filed: Sep. 22, 2009

(65) Prior Publication Data

US 2010/0076186 A1 Mar. 25, 2010

(30) Foreign Application Priority Data

Sep. 23, 2008 (EP) .................................... 08164919
Jul. 7, 2009 (EP) .................................... 09164707

(51) Int. Cl.
*C07D 413/00* (2006.01)

(52) U.S. Cl. ........................................................ 544/96

(58) Field of Classification Search .................. None
See application file for complete search history.

(56) References Cited

U.S. PATENT DOCUMENTS

| | | | |
|---|---|---|---|
| 4,806,267 A | 2/1989 | Culbertson et al. | |
| 2008/0207838 A1 | 8/2008 | Omeis et al. | |

FOREIGN PATENT DOCUMENTS

| | | |
|---|---|---|
| DE | 2153513 A1 | 5/1971 |
| DE | 2135644 A1 | 2/1973 |
| EP | 1 548 012 A3 | 6/2005 |
| EP | 1548012 A2 | 6/2005 |
| GB | 1369129 A | 10/1974 |
| GB | 1411640 | 10/1975 |

OTHER PUBLICATIONS

Jnaneshwara. Tetrahedron Letters, 1998, 39, 459-462.*
Lixin. Journal of Materials Sciences Letters, 2003, 22, 953-954.*
Mohammadpoor-Baltork. Catalysis Communications, 2008, 9, 894-901.*
Bill M. Culbertson, "Cyclic imino ethers in step-growth polymerizations", Progress in Polymer Science 27 (2002), pp. 579-626.
U.S. Appl. No. 12/990,371, filed Oct. 29, 2010, Omeis, et al.
U.S. Appl. No. 12/990,421, filed Oct. 29, 2010, Omeis, et al.

* cited by examiner

*Primary Examiner* — Noble Jarrell
(74) *Attorney, Agent, or Firm* — Oblon, Spivak, McClelland, Maier & Neustadt, L.L.P.

(57) ABSTRACT

Provided is a process for preparing a heterocycle by catalytic reaction of an aromatic dinitrile with an amino alcohol, wherein the process includes: initially charging into a reaction vessel the amino alcohol and a catalyst to produce a reaction mixture; adding the aromatic dinitrile into the reaction mixture, which is maintained at a reaction temperature, wherein no solvent other than the amino alcohol of formula (III) is added to the reaction mixture prior to and/or during the catalytic reaction; and after completion of the catalytic reaction, completely replacing, or substantially completely replacing, unreacted amino alcohol with a nonpolar solvent to obtain the heterocycle, wherein the unreacted amino alcohol is present in an amount of not more than 20 wt. %, preferably 3-10 wt. % or less, based on a total weight of the heterocycle.

20 Claims, No Drawings

PROCESS FOR PREPARING HETEROCYCLES

CROSS-REFERENCE TO RELATED APPLICATIONS

The present application claims priority to European patent applications EP 08164919, filed on Sep. 23, 2008, and EP 09164707, filed on Jul. 7, 2009, the contents of which are incorporated herein by reference in their entireties.

BACKGROUND OF THE INVENTION

1. Field of the Invention

The present invention relates to a process for preparing a heterocycle by catalytic reaction of an aromatic dinitrile and an amino alcohol.

2. Discussion of the Background

DE 2135644 describes a non-catalytic process for preparing cyclic imidic esters from aromatic nitriles and amino alkanols, wherein the process has a reaction time of more than 20 hours. The reaction is carried out under a protective gas in order to suppress by-product formation. The reaction mixture is worked up by methods including recrystallization.

DE 2153513 describes a process for preparing oxazines from N,N'-bis(3-halopropyl)dicarboxamides or bis(3-halopropyl)dicarboximidates in the presence of a base. The reaction mixture is worked up by recrystallization.

U.S. Pat. No. 4,806,267 describes a process for preparing a mixture of bisoxazines by reacting mixtures of amino alkanols with dinitriles in the presence of a cadmium nitrate catalyst or a zinc acetate catalyst, and xylene as a solvent. The reaction time is 10 or 20 hours.

Culbertson, B. M., Cyclic Imino Ethers in Step-Growth Polymerization, Progress of Polymer Science, 27, 579-626 (2002), describes the synthesis of oxazines by the reaction of nitriles and amino alcohols in the presence of a zinc acetate catalyst and xylene as a solvent.

EP 1548012 describes a catalytic process for preparing phenylenebisoxazolines by reaction of terephthalonitrile or isophthalonitrile with 1,2-amino alcohols in the presence of a zinc catalyst and xylene as a solvent. The reaction may be carried out in the absence of an additional solvent (e.g., xylene).

SUMMARY OF THE INVENTION

The present invention relates to a process for preparing a heterocycle by catalytic reaction of an aromatic dinitrile and an amino alcohol.

An exemplary aspect of the present invention relates to a process for preparing a heterocycle of the following formula (I) by catalytic reaction of an aromatic dinitrile of the following formula (II) with an amino alcohol of the following formula (III):

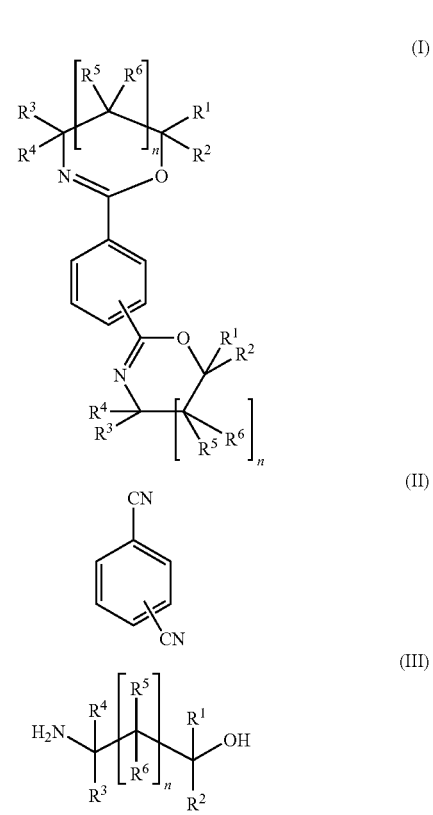

wherein $R^1$, $R^2$, $R^3$, $R^4$, $R^5$ and $R^6$, may be the same or different, and are each independently selected from the group consisting of a hydrogen atom, an alkyl group, an aryl group, a —COOH group and an —NH$_2$ group, and n is an integer of from 0 to 4, preferably from 1 to 4, more preferably from 1 to 3, and most preferably from 1 to 2, wherein the process comprises:

initially charging into a reaction vessel the amino alcohol of formula (III) and a catalyst to produce a reaction mixture;

adding the aromatic dinitrile of formula (II) into the reaction mixture which is maintained at a reaction temperature, wherein no solvent other than the amino alcohol of formula (III) is added to the reaction mixture prior to and/or during the catalytic reaction; and after completion of the catalytic reaction, completely replacing, or substantially completely replacing, unreacted amino alcohol of formula (III) with a nonpolar solvent to obtain the heterocycle of formula (I), wherein unreacted amino alcohol of formula (III) is present in an amount of not more than 20 wt. %, based on a total weight of the heterocycle of formula (I).

Another exemplary aspect of the present invention is to provide a process for preparing a heterocycle of formula (I) by catalytic reaction of an aromatic dinitrile of formula (II) with an amino alcohol of formula (III), wherein the process is able to be carried out with shorter processing times and improved yields, which is particularly advantageous when performing the process of the present invention on an industrial scale.

Another exemplary aspect of the present invention is to provide a process for preparing a heterocycle of formula (I) by catalytic reaction of an aromatic dinitrile of formula (II) with an amino alcohol of formula (III), wherein the process enables effective removal of the heterocycle of formula (I)

from the reaction mixture, which may contain higher homologues of excess unreacted amino alcohol of formula (III).

Another exemplary aspect of the present invention is to provide a process for preparing the heterocycle of formula (I) by catalytic reaction of an aromatic dinitrile of formula (II) with an amino alcohol of formula (III), wherein the process provides for the recycling of excess starting materials, reagents and/or solvents, including, but not limited to, excess unreacted amino alcohol of formula (III).

DETAILED DESCRIPTION OF THE INVENTION

Unless specifically defined, all technical and scientific terms used herein have the same meaning as commonly understood by a skilled artisan in the relevant technological field (e.g., organic chemistry, inorganic chemistry, chemical engineering).

All processes, materials and examples similar or equivalent to those described herein can be used in the practice or testing of the present invention, with suitable processes, materials and examples being described herein. Accordingly, the processes, materials and examples described herein are of illustrative purposes only and are therefore not intended to be limiting, unless otherwise specified.

Where a closed or open-ended numerical range is described herein, all values and subranges within or encompassed by the numerical range are specifically included as belonging to the original disclosure of the present application as if these values and subranges had been explicitly written out in their entirety.

The present invention provides a process for preparing a heterocycle of the following formula (I) by catalytic reaction of an aromatic dinitrile of the following formula (II) with an amino alcohol of the following formula (III):

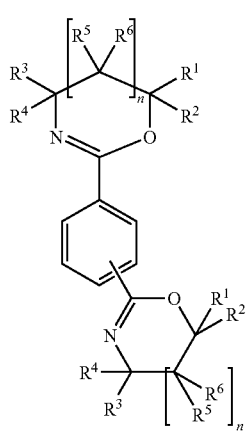

(I)

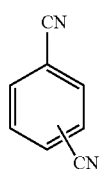

(II)

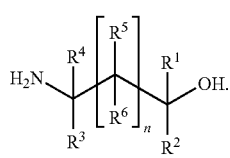

(III)

wherein $R^1$, $R^2$, $R^3$, $R^4$, $R^5$ and $R^6$, may be the same or different, and are each independently selected from the group consisting of a hydrogen atom, an alkyl group, an aryl group, a —COOH group and an —NH$_2$ group, and n is an integer of from 0 to 4, preferably from 1 to 4, more preferably from 1 to 3, and most preferably from 1 to 2, wherein the process comprises:

initially charging into a reaction vessel the amino alcohol of formula (III) and a catalyst to produce a reaction mixture;

adding, preferably metering, the aromatic dinitrile of formula (II) into the reaction mixture which is maintained at a reaction temperature, wherein no solvent other than the amino alcohol of formula (III) is added to the reaction mixture prior to and/or during the catalytic reaction; and after completion of the catalytic reaction, completely replacing, or substantially completely replacing, unreacted amino alcohol of formula (III) with a nonpolar solvent to obtain the heterocycle of formula (I), wherein unreacted amino alcohol of formula (III) is present in an amount of not more than 20 wt. %, based on a total weight of the heterocycle of formula (I).

The process of the present invention is performed without the addition of an additional solvent prior to and/or during the catalytic reaction, as the amino alcohol of formula (III) is present in the reaction mixture in an excess amount, thereby allowing the amino alcohol of formula (III) to act both as a reactant and the solvent. The presence of an excess amount of the amino alcohol of formula (III) enables efficient stirring of the reaction mixture under the process conditions.

The present invention provides a process for preparing a heterocycle of formula (I), especially oxazines, by catalytic reaction of an aromatic dinitrile of formula (II) with an amino alcohol of formula (III), wherein the process of the present invention is able to be carried out on an industrial scale with surprisingly shorter processing times (e.g., less than 10 hours) and unexpectedly improved yields (e.g., at least 75%).

In contrast to preparing phenylenebisoxazolines, the work up of reaction mixtures comprising higher homologues of the amino alcohol of formula (III) has traditionally been exceptionally difficult. The reaction mixtures of conventional processes frequently undergo gelation toward the end of the catalytic reaction, such that isolation of the heterocycle of formula (I), by filtration for example, is impossible. In other cases, the heterocycle of formula (I) forms a very finely distributed precipitate in the reaction mixture, which requires exceptionally long filtration periods and oftentimes results in clogging of the filter, which is economically impractical for industrial scale manufacturing processes.

Applicants have discovered that obtaining the heterocycle of formula (I) from the work up of a reaction mixture having higher homologues of the amino alcohol of formula (III) present therein is surprisingly simplified by replacing all, or substantially all, of the unreacted amino alcohol of formula (III) with a suitable nonpolar solvent following completion of the catalytic reaction, wherein the unreacted amino alcohol of formula (III) is present in a residual amount of not more than 20 wt. %, based on a total weight of the heterocycle of formula (I).

The heterocycle of formula (I) can then be crystallized out of the nonpolar solvent, and isolated by customary methods known to those of ordinary skill in the art, including, but not limited to, filtration, for example. An important aspect of the process of the present invention is to conduct crystallization and/or filtration of the heterocycle of formula (I) in the complete absence, or a substantially low concentration, of the amino alcohol of formula (III), because unlike phenylenebisoxazolines, there is not sufficient crystal formation of the heterocycle of formula (I) in the presence of higher homologues of the amino alcohol of formula (III).

Therefore, the present invention provides a process for preparing the heterocycle of formula (I) by catalytic reaction of an aromatic dinitrile of formula (II) with an amino alcohol of formula (III), wherein the process enables effective removal of the heterocycle of formula (I) from a reaction mixture containing higher homologues of unreacted amino alcohol of formula (III).

The present invention also provides a process for preparing the heterocycle of formula (I) by catalytic reaction of an aromatic dinitrile of formula (II) with an amino alcohol of formula (III), wherein excess starting materials, reagents and/or solvents, including, but not limited to, excess unreacted amino alcohol of formula (III), may be recycled.

The amino alcohol of formula (III) is a compound wherein n is an integer of from 0 to 4, preferably from 1 to 4, more preferably from 1 to 3, and most preferably from 1 to 2. "Higher homologues" of the amino alcohol of formula (III) is understood in the context of the present invention to mean that n is an integer of from 1 to 4. The $R^1$, $R^2$, $R^3$, $R^4$, $R^5$ and $R^6$ substituents of the amino alcohol of formula (III), may be the same or different, and are each independently selected from the group consisting of a hydrogen atom, an alkyl group, an aryl group, a —COOH group and an —NH$_2$ group. The $R^1$, $R^2$, $R^3$, $R^4$, $R^5$ and $R^6$ substituents of the amino alcohol of formula (III) are preferably a hydrogen atom, or a branched or unbranched alkyl group having from 1 to 4 carbon atoms. The $R^1$, $R^2$, $R^3$, $R^4$, $R^5$ and $R^6$ substituents of the amino alcohol of formula (III) are more preferably each a hydrogen atom. The amino alcohol of formula (III) is preferably 2-amino-1-ethanol (n=0), 3-amino-1-propanol (n=1), 4-amino-1-butanol (n=2), 5-amino-1-pentanol (n=3), and 6-amino-1-hexanol (n=4), more preferably 3-amino-1-propanol and 4-amino-1-butanol, and most preferably 3-amino-1-propanol.

It is possible to use either one amino alcohol of formula (III) or a mixture of two or more different amino alcohols of formula (III). Since the amino alcohol of formula (III) serves both as a reactant and as the solvent during the catalytic reaction, it is advantageous to use only one amino alcohol of formula (III) rather than a mixture of two or more different amino alcohols of formula (III). As a result, the process of the present invention provides for the selective preparation of a single heterocycle of formula (I), or a mixture of two or more heterocycles of formula (I).

The following formula represents an exemplary heterocycle of formula (I) obtained by catalytic reaction of an aromatic dinitrile of formula (II) with 3-amino-1-propanol as the amino alcohol of formula (III):

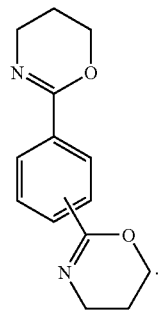

The following formula represents an exemplary heterocycle of formula (I) obtained by catalytic reaction of an aromatic dinitrile of formula (II) with 4-amino-1-butanol as the amino alcohol of formula (III):

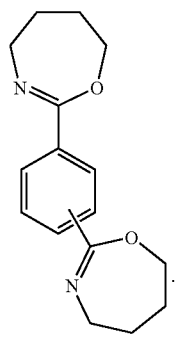

Applicants have discovered that zinc compound catalysts are particularly advantageous for the process according to the present invention. It is possible to use either a single zinc compound catalyst or a mixture of two or more zinc compound catalysts in the process according to the present invention. Preference is given to using a zinc carboxylate catalyst of a saturated, branched or unbranched, aliphatic carboxylic acid having from 2 to 10 carbon atoms. Representative examples of the zinc carboxylate catalyst include, but are not limited to, zinc acetate, zinc propionate, zinc n-butyrate, zinc isobutyrate, and zinc 2-ethylhexanoate, which may be used individually or as a mixture of two or more. Preference is given to using zinc carboxylate catalysts because these catalysts offer the simultaneous advantages of high catalytic activity, good availability, minimum toxicity and ease of handling.

Particular preference is given to zinc 2-ethylhexanoate as the catalyst for the process according to the present invention. An advantageous aspect of using zinc 2-ethylhexanoate as the catalyst for the process of the present invention is that zinc 2-ethylhexanoate is a liquid catalyst which exhibits a good solubility in the reaction mixture. As a result, the zinc 2-ethylhexanoate catalyst remains in the mother liquor after filtration and is therefore completely removed, or substantially completely removed, from the heterocycle of formula (I) in a simple manner without requiring an additional process step in the work up of the reaction mixture. Other zinc compound catalysts, including zinc acetate, for example, are sparingly soluble in the reaction mixture of the process according to the present invention, such that, when they are used, an additional process step is required in the work up of the reaction mixture, in order to remove the zinc compound catalyst from the heterocycle of formula (I).

In the process according to the present invention, the amino alcohol of formula (III) and the catalyst are initially charged into a reactor to produce a reaction mixture, and the aromatic dinitrile of formula (II) is added, preferably metered, into the reaction mixture which is maintained at a reaction temperature, wherein no solvent other than the amino alcohol of formula (III) is added to the reaction mixture prior to and/or during the catalytic reaction. The aromatic dinitrile of formula (II) is preferably added to the reaction mixture continuously over a prolonged period of time of from 1 to 4 hours, including for example, from 1.25 to 3.75 hours, from 1.50 to 3.50 hours, from 1.75 to 3.25 hours, from 2.00 to 3.00 hours, from 2.25 to 2.75 hours, and preferably from 2 to 3 hours. As a result, the concentration of the aromatic dinitrile of formula (II) in the reaction mixture remains low during the course of the entire catalytic reaction, and the evolution of an offgas comprising ammonia can be efficiently controlled, which is particularly advantageous when performing the process of the present invention on an industrial scale.

In the process according to the present invention, the aromatic dinitrile of the formula (II) can be added as a solid or as a melt to the reaction mixture comprising, predominately comprising (more than 50 wt. %), consisting essentially of, or consisting of the amino alcohol of formula (III) and the catalyst. It is possible to use either a single aromatic dinitrile of formula (II) or a mixture of two or more different aromatic dinitriles of formula (II). Representative examples of the aromatic dinitrile of formula (II) include, but are not limited to, 1,3-dinitrile and 1,4-dinitrile, which may be used individually or as a mixture.

A molar ratio of the aromatic dinitrile of formula (II) to the amino alcohol of formula (III) in the process according to the present invention is at least 1:2, including, but not limited to, 1:3, 1:4, 1:5, 1:6, 1:7, 1:8, 1:9, and 1:10, preferably 1:4-10, and more preferably 1:7-9.

A stoichiometric excess of the amino alcohol of formula (III) relative to the aromatic dinitrile of formula (II) in the reaction mixture allows the amino alcohol of formula (III) to serve both as a reactant and the solvent, thereby making it possible to dispense with adding an additional solvent (e.g., xylene) to the reaction mixture prior to and/or during the catalytic reaction. The catalytic reaction is thus performed in accordance with the process of the present invention without the addition (i.e., in the absence) of an additional solvent. Since the amino alcohol of formula (III) serves as the solvent in the reaction mixture, the catalytic reaction in accordance with the process of the present invention is allowed to be performed at a higher reaction temperature, whereby the reaction mixture advantageously does not boil when the reaction mixture is below the boiling temperature of the amino alcohol of formula (III).

Unlike the catalytic reaction according to the process of the present invention, the catalytic reaction of conventional processes are frequently performed in the presence of xylene as a solvent. A disadvantage of using xylene as a solvent is that xylene and some amino alcohols of formula (III) combine to form azeotropes with a boiling point minimum, such that the reaction mixture undesirably boils during the catalytic reaction and also during the addition of the dinitrile, thereby restricting the maximum reaction temperature for carrying out the catalytic reaction and requiring technical solutions for the addition of the dinitrile, which is in the form of a solid or a melt.

In accordance with the process of the present invention, the reaction mixture having an amino alcohol of formula (III) as the only solvent contained therein prior to and during the catalytic reaction is maintained at a reaction temperature of from 50° C. to 200° C., including, but not limited to, 55-195° C., 60-190° C., 65-185° C., 70-180° C., 75-175° C., 80-170° C., 85-165° C., 90-160° C., 95-155° C., 100-150° C., 105-145° C., 110-140° C., 115-135° C., 120-130° C., 125° C., preferably from 110° C. to 170° C., and more preferably from 130° C. to 150° C.

Surprisingly shorter reactions times and unexpectedly improved yields are remarkably obtained by dispensing with the addition of an additional solvent (e.g., xylene) to the reaction mixture prior to and/or during the catalytic reaction in accordance with the process of the present invention. In addition, the process of the present invention provides for an exceptionally simplified work up of the reaction mixture when obtaining the heterocycle of formula (I).

In accordance with an exemplary aspect of the process of the present invention, the catalytic reaction is carried out under atmospheric pressure or a reduced pressure. The catalytic reaction may be carried out at a pressure of from 0.5 bar to 10 bar, including, but not limited to, 1.0-9.5 bar, 1.5-9.0 bar, 2.0-8.5 bar, 2.5-8.0 bar, 3.0-7.5 bar, 3.5-7.0 bar, 4.0-6.5 bar, 4.5-6.0 bar, 5.0-5.5 bar; preferably from 0.6 bar to 1.5 bar, including, but not limited to, 0.7-1.4 bar, 0.8-1.3 bar, 0.9-1.2 bar, 1.0-1.1 bar; and more preferably from 0.7 bar to 1.2 bar.

In accordance with an exemplary aspect of the process of the present invention, the catalytic reaction is carried out under a slightly reduced pressure of from 0.6 bar to 0.9 bar, preferably from 0.7 bar to 0.9 bar, and more preferably from 0.8 bar to 0.9 bar. This slightly reduced pressure relative to atmospheric pressure provides for easier removal of an offgas comprising ammonia which forms as a by-product during the catalytic reaction.

The catalytic reaction of the aromatic dinitrile of formula (II) with the amino alcohol of formula (III) can be performed in a batchwise, a semicontinuous, or a continuous manner, which is flexible according to technical prerequisites, thereby constituting an additional advantage of the process of the present invention.

In accordance with an exemplary aspect of the process of the present invention, after a final addition of the aromatic dinitrile of formula (II) into the reaction mixture, the reaction mixture is advantageously maintained at a reaction temperature, preferably under stirring, for a postreaction period of 1-5 hours, including, but not limited to, 1.25-4.75 hours, 1.50-4.50 hours, 1.75-4.25 hours, 2.0-4.0 hours, 2.25-3.75 hours, 2.50-3.50 hours, 2.75-3.25 hours, and 3.00 hours, preferably 2-4 hours. The exact duration of the postreaction period can be determined by a continuous analysis (e.g., gas chromatography) of the offgas, whereby the absence of ammonia in the offgas indicates cessation in the production of ammonia by-product and thus the completion of the catalytic reaction.

A total reaction time of the catalytic reaction in accordance with the process of the present invention, which includes the addition of the reactants and the postreaction period, is less than 10 hours and is dependent on the reaction temperature. The total reaction time of the catalytic reaction is less than 10 hours, preferably from 2 to 9 hours, including, but not limited to, 2.25-8.75 hours, 2.50-8.50 hours, 2.75-8.25 hours, 3.00-8.00 hours, 3.25-7.75 hours, 3.50-7.50 hours, 3.75-7.25 hours, 4.00-7.00 hours, 4.25-6.75 hours, 4.50-6.50 hours, 4.75-6.25 hours, 5.00-6.00 hours, 5.25-5.75 hours and 5.5 hours. At a reaction temperature of 110-170° C., the total reaction time of the catalytic reaction in accordance with the process of the present invention is from 4 to 8 hours, and preferably from 5 to 7 hours. This surprisingly short total reaction time of the catalytic reaction in accordance with the process of the present invention significantly lowers production costs, which is particularly advantageous when producing heterocycles on an industrial scale, thereby representing another distinct advantage over conventional processes, which require significantly longer reaction times of from 20 to 25 hours, which increase production costs.

In accordance with the process of the present invention, after completion of the catalytic reaction (e.g., following the postreaction period), excess unreacted amino alcohol of formula (III) is completely removed, or substantially completely removed, by distillation, for example.

In accordance with the process of the present invention, 40-70 wt. %, 45-65 wt. %, 50-60 wt. %, preferably 40-70 wt. %, and more preferably 55-65 wt. %, of unreacted amino alcohol of formula (III) is removed by distillation, which may be carried out under a reduced pressure, including, for example, 75-400 mbar, 100-375 mbar, 125-350 mbar, 150-325 mbar, 175-300 mbar, 200-375 mbar, 225-350 mbar, 250-325 mbar, 275-300 mbar, preferably 100-300 mbar.

In accordance with the process of the present invention, a residual proportion of unreacted amino alcohol of formula (III), which still remains in the reaction mixture following distillation after completion of the catalytic reaction, is completely removed, or substantially completely removed, by a subsequent distillation that is carried out in the presence of a nonpolar solvent. The subsequent distillation may also be carried out under a reduced pressure, including, for example, the distillative reduced pressures described hereinabove with respect to the distillation.

"Substantially complete removal" of the unreacted amino alcohol of formula (III) is understood in the context of the present invention to mean that the unreacted amino alcohol of formula (III) is present in the reaction mixture, following the distillative removal thereof, in an amount of not more than 20 wt. %, including 1-19 wt. %, 2-18 wt. %, 3-17 wt. %, 4-16 wt. %, 5-15 wt. %, 6-14 wt. %, 7-13 wt. %, 8-12 wt. %, 9-11 wt. %, and more preferably 3-10 wt. %, based on a total weight of the heterocycle of formula (I).

"Complete removal" of the unreacted amino alcohol of formula (III) is understood in the context of the present invention to mean that the unreacted amino alcohol of formula (III) is present in the reaction mixture, following the distillative removal thereof, in an amount of less than 1 wt. %, less than 0.75 wt. %, less than 0.50 wt. %, less than 0.25 wt. %, and preferably less than 0 wt. %, based on a total weight of the heterocycle of formula (I).

The nonpolar solvent is added, preferably continuously metered, into the reaction mixture after completion of the catalytic reaction, while the residual proportion of unreacted amino alcohol of formula (III) is simultaneously removed during the subsequent distillation. Particular preference is given to metering into the reaction mixture an amount of the nonpolar solvent that is equal to the volume of distillate collected, which comprises, predominately comprises (more than 50 wt. %), consists essentially of, or consists of the residual portion of unreacted amino alcohol of formula (III) and the nonpolar solvent, which may have been entrained during the subsequent distillation. The nonpolar solvent present in the reaction mixture after completion of the catalytic reaction then serves, in place of the amino alcohol of formula (III), as a solvent and/or a suspension medium for the heterocycle of formula (I). The residual proportion of unreacted amino alcohol of formula (III) and/or the nonpolar solvent which is/are present in the distillate may then be recycled directly, or after further purification and/or separation, into various stages of the process of the present invention.

Suitable nonpolar solvents are those which are inert towards the amino alcohol of formula (III) and the heterocycle of formula (I), and have a boiling point of at least 100° C., including, for example, 100-150° C., 105-145° C., 110-140° C., 115-135° C., 120-130° C., preferably 115-145° C., and more preferably 125-135° C. Aromatic solvents including toluene, ethylbenzene, o-, m- and/or p-xylene, and mixtures thereof, represent non-limiting examples of suitable nonpolar solvents. Preference is given to nonpolar solvents which combine with the amino alcohol of formula (III) to form an azeotrope with a boiling point minimum. Particular preference is given to xylene as the nonpolar solvent, which forms an azeotrope with 3-amino-1-propanol as the amino alcohol of formula (III).

As a result of the distillative removal of unreacted amino alcohol of formula (III) from the reaction mixture, a heterocycle of formula (I) is obtained, wherein the unreacted amino alcohol of formula (III) is present in an amount of not more than 20 wt. %, preferably 0-20 wt. %, 1-19 wt. %, 2-18 wt. %, 3-17 wt. %, 4-16 wt. %, 5-15 wt. %, 6-14 wt. %, 7-13 wt. %, 8-12 wt. %, 9-11 wt. %, and more preferably 3-10 wt. %, based on a total weight of the heterocycle of formula (I), whereby the crude product of the heterocycle of formula (I) can then be efficiently crystallized.

As a result of the complete absence, or substantially complete absence, of the amino alcohol of formula (III) present in the crude product of the heterocycle of formula (I) produced by the process of the present invention, two liquid phases do not form, in contrast to the process according to EP 1548012. Accordingly, the utilization of solubilizers (e.g., alcohols), other than the amino alcohol of formula (III), can be dispensed with in the process of the present invention. Dispensing with solubilizers has the advantage that removing unreacted amino alcohol of formula (III) is comparatively simple relative to the process described in EP 1548012, which utilizes an isopropanol solubilizer that forms an azeotrope with some amino alcohols of formula (III).

In accordance with the process of the present invention, the heterocycle of formula (I) is able to be crystallized out of the crude reaction product and, in contrast to conventional processes, easily obtained by customary isolation techniques known to those of ordinary skill in the art, including filtration, for example. Accordingly, the process of the present invention enables the heterocycle of formula (I) to be easily filtered off in a relative short period of time without clogging of the filter. Owing to the air sensitivity of the heterocycles of the formula (I), the filtration is preferably performed under an inert atmosphere, preferably a nitrogen atmosphere.

The mother liquor which remains after the filtration can be recycled into various stages of the process of the present invention, including the work up of the crude reaction product present in the reaction following completion of the catalytic reaction, for example. Preferably, the mother liquor is recycled into the process of the present invention at a point upstream of the distillation or subsequent distillation of unreacted amino alcohol of formula (III), alone or in combination with the nonpolar solvent. The mother liquor may also be used in combination with or as a replacement of the nonpolar solvent. The recycling of the mother liquor provides for further enhanced yields. The recycling of the mother liquor in accordance with an exemplary aspect of the present invention is simplified significantly as compared to the process described in EP 1548012, since the mother liquor of the present invention comprises, predominantly comprises, consists essentially of or consists of the nonpolar solvent. As a result, no complicated work up is needed in order to recycle the mother liquor of the present invention, especially since a solubilizer (e.g., alcohol) is preferably dispensed with, unlike the process described in EP 1548012.

When the catalyst used in the catalytic reaction of the process according to the present invention is zinc 2-ethylhexanoate, the catalyst remains in the mother liquor, thereby providing a simple manner for removing the catalyst from the heterocycle of formula (I) and enabling high purity crystals of the heterocycle of formula (I) to be obtained. This has the added advantage that a further work up step for removing the catalyst from the heterocycle of formula (I) is not required, thereby shortening processing times and reducing production costs, which is particularly advantageous when performing the process of the present invention on an industrial scale.

The crystals of the heterocycle of formula (I) are repeatedly washed, preferably with one or more alcohols having 1 to 4 carbon atoms, preferably methanol, ethanol, isopropanol or mixtures thereof, more preferably with methanol, and dried under a reduced pressure, preferably 10-25 mbar, at a temperature of 80-100° C. for a period of 3-5 hours.

When a sparingly soluble zinc compound (e.g., zinc acetate) has been used as the catalyst in the catalytic reaction of the process according to the present invention, the crystals of the heterocycle of the formula (I) are preferably washed first with water in order to remove the catalyst. Thereafter, the crystals of the heterocycle of the formula (I) are washed with the alcohol.

The heterocycles of formula (I) obtained by the process according to the present invention can be used, for example, as chain extenders or crosslinkers in polymers (See e.g., U.S. Pat. No. 4,806,267 and Culbertson, B. M., Progress of Polymer Science, 27, 579-626 (2002)).

The above written description is provided to thereby enable a skilled artisan to practice the invention described and claimed herein. Various modifications to the exemplary aspects will be readily apparent to those skilled in the art, and general principles and features defined herein may be applied to other non-exemplified aspects without departing from the spirit and scope of the present invention. Thus, the present invention is not intended to be limited to the aspects exemplified herein, but is to be accorded the broadest reasonable scope consistent with the general principles and features disclosed herein.

Having generally described the present invention, a further understanding can be obtained by reference to specific examples, which are provided herein merely for illustration purposes only, and are not intended to be limiting unless otherwise specified.

EXAMPLES

Example 1

The reaction was performed in a 2 liter 4-neck stirred flask with an internal thermometer, paddle stirrer with stirrer sleeve and stirrer motor, heating with an oil bath, water separator, reflux condenser and an offgas line with a bubble counter to monitor the ammonia being released. For this purpose, 600.0 g of 3-amino-1-propanol (7.9 mol) and 5.0 g of zinc 2-ethylhexanoate (0.01 mol) were initially charged in the reaction vessel and adjusted to a temperature of approximately 140° C. with stirring. 128.0 g of terephthalonitrile (1.0 mol) was added continuously to the reaction solution in the reactor within a period of 2.5 hours. After the end of the terephthalonitrile addition, stirring was continued at 140° C. for 3.5 hours. A solution was present in the reactor. The progress of the reaction was determined via both offgas formation and GC analysis. At the end of the postreaction time, only a minimal amount of offgas formed. The reaction was performed up to a conversion of >99% of the target product.

After the reaction ended, a portion (approximately 280 g) of the excess 3-amino-1-propanol was removed by distillation under reduced pressure (approximately 150 mbar). The remaining 3-amino-1-propanol, by addition of 325 g of xylene to the reaction mixture, was substantially completely removed by a codistillation of xylene and 3-amino-1-propanol.

Subsequently, the reaction mixture was allowed to cool to 20° C. with stirring and under a nitrogen atmosphere. The crystals of the heterocycle formed were filtered off with suction through a glass suction filter, slurried on the suction filter three times in succession with methanol, and suction-dried.

The moist crystals were dried in a vacuum drying cabinet at 25 to 10 mbar and 80° C. to 100° C. for 4 hours. The product was obtained as pure white, free-flowing crystals (GC and NMR purity: >99%; melting range: 216° C. to 220° C.). The yield of the heterocycle of the formula (I) was 75%.

Comparative Example 1

The reaction was performed in a 2 liter 4-neck stirred flask with an internal thermometer, paddle stirrer with stirrer sleeve and stirrer motor, heating with an oil bath, water separator, reflux condenser and an offgas line with a bubble counter to monitor the ammonia being released. For this purpose, 600.0 g of 3-amino-1-propanol (7.9 mol) and 5.0 g of zinc 2-ethylhexanoate (0.01 mol) were initially charged in the reaction vessel and adjusted to a temperature of approx. 140° C. with stirring. 128.0 g of terephthalonitrile (1.0 mol) was added continuously to the reaction solution in the reactor within 2.5 hours. After the end of the terephthalonitrile addition, stirring was continued at 140° C. for 3.5 hours. A solution was present in the reactor. The progress of the reaction was determined both via the offgas formation and via the GC analysis. At the end of the postreaction time, only a minimal amount of offgas formed. The reaction was performed up to a conversion of >99% in the direction of the target product.

Work Up without Further Intermediate Steps:

The reaction mixture was cooled to 20° C. with stirring and under a nitrogen atmosphere. The target product—the heterocycle of formula (I)—precipitated out in very fine distribution. The filtration took about 16 hours. Even after the subsequent scrubbing with methanol, the filterability of the heterocycle of formula (I) was extremely poor.

Example 1 and Comparative Example 1 show that, in the presence of amino alcohols of formula (III), there was insufficient crystallization, and hence obtaining heterocycles of formula (I) by filtration was nearly impossible.

Example 2

The reaction was performed in a 2 liter 4-neck stirred flask with an internal thermometer, paddle stirrer with stirrer sleeve and stirrer motor, heating with an oil bath, water separator, reflux condenser and an offgas line with a bubble counter to monitor the ammonia being released. For this purpose, 600.0 g of 3-amino-1-propanol (7.9 mol) and 5.0 g of zinc 2-ethylhexanoate (0.01 mol) were initially charged in the reaction vessel and adjusted to a temperature of approx. 135° C. with stirring. 128.0 g of terephthalonitrile (1.0 mol) was added continuously to the reaction solution in the reactor within 2 hours. After the end of the terephthalonitrile addition, stirring was continued at 135° C. for 5 hours. A solution was present in the reactor. The progress of the reaction was determined both via the offgas formation and via the GC analysis. At the end of the postreaction time, only a minimal amount of offgas formed. The reaction was performed up to a conversion of >95% in the direction of the target product.

Comparative Example 2

The reaction was performed in a 2 liter 4-neck stirred flask with an internal thermometer, paddle stirrer with stirrer sleeve and stirrer motor, heating with an oil bath, water separator, reflux condenser and an offgas line with a bubble counter to monitor the ammonia being released. For this purpose, 600.0 g of 3-amino-1-propanol (7.9 mol), 325 g (3 mol) of xylene and 5.0 g of zinc 2-ethylhexanoate (0.01 mol) were initially charged in the reaction vessel and adjusted to a temperature of approx. 135° C., which established a gentle reflux. 128.0 g of terephthalonitrile (1.0 mol) was added continuously to the reaction solution in the reactor within 3 hours. After the end of the terephthalonitrile addition, stirring was continued at 135° C. for 17 hours. A solution was present in the reactor. The progress of the reaction was determined both via the offgas formation and via the GC analysis. At the end of the postreaction time, only a minimal amount of offgas formed. The reaction was performed up to a conversion of >95% in the direction of the target product.

Example 2 and Comparative Example 2 clearly show that the presence of an additional solvent during the reaction leads to a significant extension of the reaction time.

The invention claimed is:

1. A process for preparing a heterocycle of the following formula (I) by catalytic reaction of an aromatic dinitrile of the following formula (II) with an amino alcohol of the following formula (III):

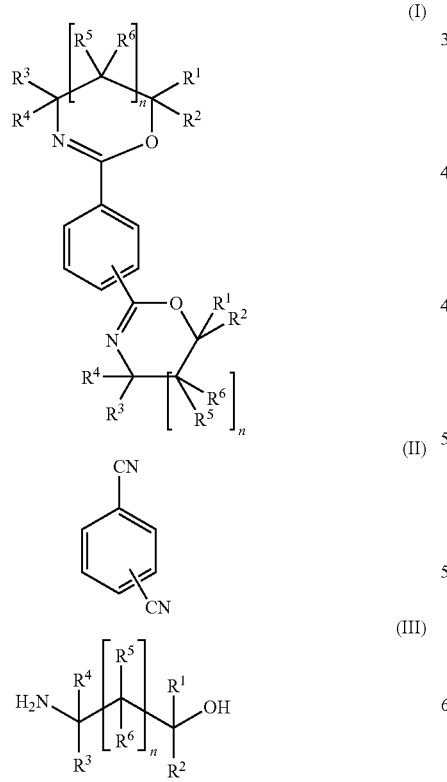

wherein $R^1$, $R^2$, $R^3$, $R^4$, $R^5$ and $R^6$, may be the same or different, and are each independently selected from the group consisting of a hydrogen atom, an alkyl group, an aryl group, a —COOH group and an —NH$_2$ group, and n is an integer of from 0 to 4, wherein said process comprises:

initially charging into a reaction vessel the amino alcohol of formula (III) and a catalyst to produce a reaction mixture;

adding the aromatic dinitrile of formula (II) into the reaction mixture, which is maintained at a reaction temperature, wherein no solvent other than the amino alcohol of formula (III) is added to the reaction mixture prior to and/or during the catalytic reaction; and after completion of the catalytic reaction, completely replacing, or substantially completely replacing, unreacted amino alcohol of formula (III) with a nonpolar solvent to obtain the heterocycle of formula (I), wherein the unreacted amino alcohol of formula (III) is present in an amount of not more than 20 wt. %, based on a total weight of the heterocycle of formula (I).

2. The process according to claim 1, wherein n is an integer of from 1 to 4.

3. The process according to claim 1, wherein the amino alcohol of formula (III) is 3-amino-1-propanol.

4. The process according to claim 1, wherein the aromatic dinitrile of formula (II) is 1,3-dinitrile and/or 1,4-dintrile.

5. The process according to claim 1, wherein the catalyst is zinc 2-ethylhexanoate.

6. The process according to claim 1, wherein the amino alcohol of formula (III) is present in the reaction mixture in a stoichiometric excess relative to the aromatic dinitrile of formula (II).

7. The process according to claim 1, wherein a molar ratio of the aromatic dinitrile of formula (II) to the amino alcohol of formula (III) is at least 1:2.

8. The process according to claim 1, wherein the aromatic dinitrile of formula (II) is metered into the reaction mixture over a period of 1-4 hours.

9. The process according to claim 1, wherein the catalytic reaction is carried out under a reduced atmospheric pressure.

10. The process according to claim 1, wherein the reaction temperature is 50-200° C.

11. The process according to claim 1, wherein the reaction mixture is maintained at the reaction temperature for a period of 2-9 hours.

12. The process according to claim 1, further comprising:

after completion of the catalytic reaction, removing 40-70 wt. % of unreacted amino alcohol of formula (III) from the reaction mixture by a distillation; and following the distillation after completion of the catalytic reaction, a residual portion of the amino alcohol of formula (III) remaining in the reaction mixture is completely removed, or substantially completely removed, by a subsequent distillation carried out with the addition of a nonpolar solvent.

13. The process according to claim 12, wherein the distillation and the subsequent distillation are carried out under a pressure of 75-400 mbar.

14. The process according to claim 12, wherein the nonpolar solvent is xylene.

15. The process according to claim 12, wherein unreacted amino alcohol of formula (III) is present in the reaction mixture in an amount of not more than 20 wt. %, based on a total weight of the heterocycle of formula (I), following the subsequent distillation.

16. The process according to claim 12, wherein unreacted amino alcohol of formula (III) is present in the reaction mixture in an amount of 3-10 wt. %, based on a total weight of the heterocycle of formula (I), following the subsequent distillation.

17. The process according to claim 12, further comprising:
filtration of the reaction mixture to obtain crystals of the heterocycle of formula (I) and a mother liquor.

18. The process according to claim 17, wherein the filtration is carried out under an inert atmosphere.

19. The process according to claim 17, further comprising:
washing the crystals of the heterocycle of formula (I) with a $C_1$-$C_4$ alcohol after an optional washing with water.

20. The process according to claim 17, further comprising:
recycling the mother liquor into the process before the subsequent distillation, wherein the mother liquor is used in combination with or in place of the nonpolar solvent during the subsequent distillation.

* * * * *